United States Patent [19]

Burton et al.

[11] Patent Number: 5,061,818
[45] Date of Patent: Oct. 29, 1991

[54] PROCESS FOR TRANSHALOGENATING A HALOPHOSPHORUS COMPOUND WITH FLUORIDE

[75] Inventors: Lester P. J. Burton; Meng-Sheng Ao, both of Baton Rouge, La.

[73] Assignee: Ethyl Corporation, Richmond, Va.

[21] Appl. No.: 110,198

[22] Filed: Oct. 19, 1987

[51] Int. Cl.$^5$ .............................................. C07F 9/141
[52] U.S. Cl. ..................................... 558/84; 558/90; 558/140
[58] Field of Search ........................... 558/84, 90, 140

[56] References Cited

U.S. PATENT DOCUMENTS

| 3,254,050 | 5/1966 | Baranauckas et al. | 260/45.7 |
| 3,281,506 | 10/1966 | Shephard et al. | 558/96 |
| 4,094,855 | 6/1978 | Spivack | 558/195 |
| 4,233,207 | 11/1980 | Spivack | 558/195 |

*Primary Examiner*—Margaret B. Medley
*Attorney, Agent, or Firm*—Joseph D. Odenweller

[57] ABSTRACT

Phosphorus compounds having at least one chlorine, bromine or iodine bonded directly to phosphorus are transhalogenated with fluorine by reaction with a fluoride salt, e.g., KF, or ammonium fluoride in the presence of a hydrogen halide salt of a pyridine-type nitrogen base, e.g., pyridine hydrochloride.

23 Claims, No Drawings

PROCESS FOR TRANSHALOGENATING A HALOPHOSPHORUS COMPOUND WITH FLUORIDE

BACKGROUND

It is known that fluorine can be exchanged for chlorine, bromine or iodine bonded to phosphorus by reaction of the halophosphorus compound with a metal fluoride. The transhalogenation reaction is quite slow and difficult to push to completion. It is sometimes desirable to replace chlorine, bromine, or iodine bonded to phosphorus with a fluorine atom. For example, Burton U.S. Ser. No. 020,023 filed Feb. 27, 1987 describes a family of hydrocarbylfluorophosphites that are very effective stabilizers in polyolefins, especially in combination with phenolic antioxidants, and are also hydrolytically stable. These compounds are made by first forming a hydrocarbyl chlorophosphite by reaction of an appropriate aliphatic or aromatic hydroxy compound with $PCl_3$ to form a mono or dichlorophosphite and then transhalogenating the chlorine atom with fluorine by reaction with a metal fluoride such as potassium fluoride. In view of the exceptional properties of these fluorophosphites, a need exists for an improved synthetic method.

SUMMARY OF THE INVENTION

It has now been discovered that the transhalogenation of of a chlorine, bromine or iodine atom bonded directly to phosphorus by reaction with a fluoride salt can be sharply promoted by including in the reaction mixture a hydrogen halide salt of a pyridine-type compound.

DESCRIPTION OF THE PREFERRED EMBODIMENTS

A preferred embodiment of the invention is a process for exchanging a halogen bonded to a phosphorus atom with fluorine said process comprising reacting a phosphorus compound having a halogen selected from chlorine, bromine or iodine bonded directly to phosphorus with a fluoride salt in the presence of a hydrogen halide salt of a pyridine-type compound.

The phosphorus bound halogen that is exchanged with fluorine can be chlorine, bromine or iodine. The exchange is more difficult with chlorine but phosphorus bound chlorine compounds are the most readily available. Accordingly the preferred phosphorus bound halogen is chlorine.

The fluoride salt can be any metal fluoride capable of transhalogenating phosphorus bound chlorine, bromine or iodine. These include LiF, NaF, KF, RbF, $CaF_2$, CsF, $SbF_3$, $KHF_2$, AgF, $HgF_2$, $CoF_3$, $SnF_4$ and the like. Likewise other fluoride salts such as an ammonium fluoride can be used. The more preferred fluorides are the alkali metal fluorides such NaF and especially KF.

The amount of fluoride salt should be at least a stoichiometric amount. In general, use of about 1-10 equivalents of fluoride per equivalent of phosphorus bound halogen is recommended. More preferably the amount of fluoride is about 1-5 equivalents and most preferably 1.1-2 equivalents per equivalent of phosphorus bound halogen.

The fluoride salt should be in finely divided form to present a high surface area since the reaction is heterogeneous. Ground or milled metal fluoride is most useful.

The transhalogenation can be conducted in a liquid reaction medium or solvent. The preferred liquids are inert aprotic solvents such as tetrahydrofuran, benzene, toluene, xylene, heptane, octane, cyclohexane and the like. The amount of solvent is not critical and can range from about 0-100 parts by weight per part of phosphorus compound.

The transhalogenation should be conducted at a temperature high enough to cause the halogen exchange to proceed but not so high as to cause undesired degradation of the reaction products. A useful temperature range is about 20°-300° C., more preferably about 50°-200° C. and most preferably at the atmospheric pressure reflux temperature of the reaction mixture. Higher temperatures will of course require a sealed system under pressure.

The reaction time should be long enough to complete the reaction. The reaction time is much shorter than the time required to conduct the transhalogenation without the use of the pyridine-hydrogen halide promoter. The reaction is generally complete in 0.5-12 hours and in most cases in 1-2 hours.

The promoter is a hydrogen halide salt of a pyridine-type compound. Pyridine-type compounds are those compounds that include a pyridine ring in their structure. Examples of these include pyridine, alpha-picoline, beta-picoline, gamma-picoline, quinoline, isoquinoline, 7-methylquinoline, 2,3-dimethylquinoline, lepidine, quinaldine, acridine, quinolinic acid, nicotinic acid, 2-aminopyridine, 2-phenylpyridine and the like including mixtures thereof. The most preferred pyridine-compound is pyridine itself.

Hydrogen halide used to form the promoter include hydrogen chloride, hydrogen bromide and hydrogen fluoride. The most preferred hydrogen halide is hydrogen chloride and the most preferred promoter is pyridine hydrochloride.

The amount of hydrogen halide promoter should be at least a promoter amount, that is an amount that causes the transhalogenation to proceed at a higher rate. A useful range is about 0.5-50 parts by weight promoter per 100 parts of phosphorus compound. A preferred amount is about 1-20 parts promoter and more preferably about 5-15 parts promoter per 100 parts phosphorus compound.

The phosphorus compounds having chlorine, bromine or iodine bonded to phosphorus can have one or two of such halogens bonded to phosphorus. The remaining group or groups bonded to phosphorus are substituted or unsubstituted hydrocarbyl, hydrocarbyloxy or hydrocarbylthio groups. Examples of such halo phosphorus compounds are methyl dichlorophosphite, ethyl dichlorophosphite, butyl dichlorophosphite, dodecyl dichlorothiophosphite, eicosyl dichlorophosphite, triacontyl dichlorophosphite, methyl dibromophosphite, propyl dibromophosphite, hexyl diiodothiophosphite, tetradecyl diiodophosphite, eicosyl chlorobromophosphite, triacontyl bromoiodophosphite, methyl dichlorophosphate, O-ethyl dichlorothiophosphate, decyl dichlorophosphate, eicosyl dichlorophosphate, O-triacontyl dichlorothiophosphate, methyl dibromophosphate, octyl dibromophosphate, S-octadecyl dibromothiophosphate, triacontyl dibromophosphate, methyl diiodophosphate, hexadeoyl diiodophosphate, eicosyl chloroiodophosphate, O-methyl dichlorothiophosphate, O-decyl dibromothiophosphate, eicosyl diododithiophosphite, triacontyl dichlorothiophosphonate, phenyl dichlorophosphite, phenyl dibromophosphite, phenyl diiodophosphite, benzyl dichlorophosphite, benzyl dibromophosphite, methyldichlorophosphine, butyldichlorophosphine, dodecyldichlorophosphine, eicosyldibromophosphine, triacontyldiodophosphine, cyclohexyl dichlorophosphite, cyclohexyl dibromophosphite, cyclohexyl dichlorothiophosphite, cyclohexyl dibromodithiophosphate, dimethyl chlorophosphite, didodecyl chlorophosphite, dieicosyl bromophosphite, ditriacontyl iodophosphite, dimethylchlorophosphine, didodecylbromophosphine, dimethyl chlorothiophosphite, dieicosyl bromodithiophosphite, dimethyl chlorophosphate, didodecyl bromophosphate, dieicosyl bromophosphate, diphenyl chlorophosphite, diphenyl bromophosphite, diphenyl chlorophosphate, diphenyl bromotrithiophosphate, diphenyl chlorophosphate, dibenzyl chlorophosphite, dibenzyl bromophosphite, diphenyl chlorotrithiophosphate, dicyclohexyl chlorophosphate, phenyldichlorophosphine, diphenylbromophosphine, dibenzylchlorophosphine, dimethylchlorophosphine, didodecylbromophosphine, methyleicosyliodophosphine, benzyldibromophosphine and the like.

The preferred phosphorus compounds have the structure

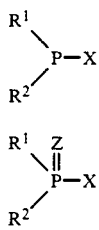

(I)

(II)

wherein X is chlorine, bromine or iodine, Z is oxygen or sulphur, $R^1$ is selected from the group consisting of substituted and unsubstituted alkoxy, thioalkoxy, aryloxy, thioaryloxy, cycloalkoxy, alkenoxy, and arylalkoxy and $R^2$ is selected from the same group as $R^1$ or is X or $R^1$ and $R^2$ can jointly form a substituted or unsubstituted divalent hydrocarbon group bonded at each end through oxygen or sulphur to the phosphorus atom in structure I or II. More preferably $R^2$ is not X.

Examples of the preferred starting phosphorus compounds are dimethyl chlorophosphite, diethyl chlorophosphite, diethyl bromophosphite, dibutyl iodophosphite, dioctyl chlorophosphite, didodecyl bromophosphite, dieicosyl iodophosphite, triacontyl dichlorophosphite, butyl dibromophosphite, methyl dodecyl chlorophosphite, eicosyl dichlorophosphite, triacontyl dibromophosphite, dimethyl chlorothiophosphite, dodecyl dibromothiophosphite, dioctadecyl chlorothiophosphite, phenyl dichlorophosphite, diphenyl bromophosphite, di(4-tert-butylphenyl) chlorophosphite, di(2,4-di-tertbutylphenyl) bromophosphite, 2-isopropyl-4-methylphenyl dichlorophosphite, di(4-tert-hexylphenyl) chlorophosphite, diphenyl chlorothiophosphite, phenyl dibromothiophosphite, 1-naphthyl dichlorophosphite, dicyclohexyl chlorophosphite, dicyclooctyl bromophosphite, cyclododecyl dichlorophosphite, dicyclohexyl bromothiophosphite, diallyl iodophosphite, di(but-2-enyl) chlorophosphite, benzyl dichlorophosphite, dibenzyl bromophosphite, di(alpha-methylbenzyl) chlorophosphite, ethyleneglycol chlorophosphite, 2,2'-methylenebis(4,6-di-tertbutylphenyl) chlorophosphite, 2,2'-methylenebis(4-methyl-6-tert-butylphenyl) bromophosphite, 2,2'bis(4,6-di-tert-butylphenyl) chlorophosphite, 2,2'bis(4,6-di-tert-butylphenyl) chlorophosphate, 2,2'ethylidenebis(4,6-di-tert-butylphenyl) chlorophosphite, 2,2'ethylidenebis(4,6-di-tert-butylphenyl) chlorophosphate, di(2,4-di-tert-butylphenyl) chlorophosphate, di(2,-6-di-tert-butylphenyl) chlorophosphite, 2,4-di-tert-butylphenyl dichlorodithiophosphate, di[4(octadecyloxycarbonylethyl)-2,6-tert-butylphenyl] chlorophosphite and the like.

In the more preferred phosphorus compounds $R^1$ and $R^2$ jointly form a divalent hydrocarbon group having the structure

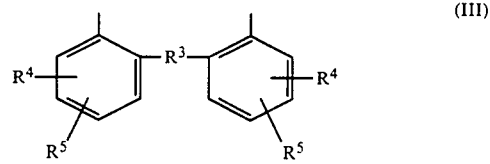

(III)

wherein $R^3$ is a methylene or alkylidene bridge or is absent forming a direct ortho-ortho bond between the benzene rings, $R^4$ and $R^5$ are independently selected from alkyl groups, cycloalkyl groups and aralkyl groups and the unsubstituted bond on each benzene ring is bonded through oxygen to said phosphorus atom in structures I or II.

Examples of phosphorus compounds which contain the above divalent hydrocarbon group are 2,2'-methylenebis(4-methyl-6-tertbutylphenyl) chlorophosphite, 2,2'-methylenebis(4-methyl-6-tertbutylphenyl) ohlorophosphate, 2,2'-methylenebis(4,6-di-tert-butylphenyl) bromophosphite, 2,2'-ethylidenebis(4-methyl-6-tert-butylphenyl) chlorophosphite, 2,2'-ethylidenebis(4-methyl-6-tert-butylphenyl) chlorophosphate, 2,2'-isopropylidenebis(4-methyl-6-tertpentylphenyl) bromophosphite, 2,2'-(butylidenebis(4,6-di-tert-butylphenyl) chlorophosphite, 2,2'-bis(4-sec-dodecyl-6-tert-butylphenyl) chlorophosphate, 2,2'-bis(4-methyl-6-tert-hexylphenyl) bromophosphite, 2,2'-bis(4-methyl-6-cyclohexylphenyl) chlorophosphate, 2,2'-ethylidenebis(4,6-dicyclohexylphenyl) chlorophosphite, 2,2'-methylenebis[4,6-di(alpha-methylbenzyl)phenyl] bromothiophosphite, 2,2'-ethylidenebis(4-methyl-6(alpha-methylbenzyl)phenyl) chlorophosphite, 2,2'-bis[4,6-di(alpha-methylbenzyl)phenyl] bromophosphite and the like.

In a highly preferred embodiment the $R^4$ groups are bonded at the 6,6'-positions and the $R^5$ groups are bonded at the 4,4'-positions in structure III. Still more preferably both $R^4$ groups are tert-alkyls having 4–12 carbon atoms and $R^5$ is $C_{1-12}$ alkyl, especially a tert-alkyl of 4–12 carbon atoms.

The most preferred phosphorus compound used as a starting material is 2,2'-ethylidenebis(4,6-di-tert-butylphenyl) chlorophosphite.

The reaction is readily carried out by placing the phosphorus compound and optionally a solvent in a stirred reaction vessel together with the finely divided fluoride salt and the pyridine or pyridine-type hydrogen halide promoter. This mixture is stirred at reaction temperature until the transhalogenation is substantially complete. The product can be recovered by conventional means such as by filtering to remove insoluble inorganic salts and then water-washing to remove residual salts and promoter. Product will usually crystallize on cooling or part of the solvent can then be removed by evaporation under vacuum followed by crystallization. Further purification of the remaining product can be achieved by conventional recrystallization.

The following examples show how the reaction is conducted.

EXAMPLE 1

The 2,2'-ethylidenebis(4,6-di-tert-butylphenyl) chlorophosphite starting material was made by heating a mixture of 100 grams 2,2'-ethylidenebis(4,6-di-tert-butylphenol), 37.6 grams PCl$_3$, 130 grams xylene and 10 grams of pyridine at reflux (140° C.) for 2 hours as described in co-pending application Ser. No. 212020 filed June 27, 1988, pending. Gas chromatographic (GC) analysis showed the reaction product excluding solvent, pyridine hydrochloride and PCl$_3$ to be 90 area percent 2,2'-ethylidenebis(4,6-di-tert-butylphenyl) chlorophosphite, 5 percent 2,2'-ethylidenebis(4,6-di-tert-butylphenyl) hydrogen phosphonate and 5 percent of two heavy impurities.

To this reaction mixture was added 20 grams KF (anhydrous finely divided high surface area) and heating continued at reflux for an additional hour. GC analysis now gave 98 area percent 2,2'-ethylidenebis(4,6-di-tert-butylphenyl) fluorophosphite, 0.2 percent of the corresponding chlorophosphite and 0.7 percent of the corresponding hydrogen phosphonate. Ammonia gas was bubbled into the reaction mixture to form NH$_4$Cl and the mixture was filtered to remove KCl, KF and NH$_4$Cl. The filtrate was cooled causing the fluorophosphite to crystallize. The product was then recovered by filtration. The yield based on initial 2,2'-ethylidenebis(4,6-di-tert-butylphenol) was 86 percent.

EXAMPLE 2

In a reaction flask was placed 100 grams of 2,2'-ethylidenebis(4,6-di-tert-butylphenol), 130 grams of mixed xylenes, 10 grams of pyridine and 38 grams of PCl$_3$. The mixture was stirred and heated to reflux while maintaining a nitrogen sweep over the reaction surface to assist in HCl removal. Stirring was continued one hour at reflux. The reaction mixture was analyzed by GC and still contained a small amount of unreacted bisphenol. An additional 3 grams of PCl$_3$ was added and reflux continued an additional 30 minutes. Conversion to 2,2'-ethylidene bis(4,6-di-tert-butylphenyl) chlorophosphite was essentially complete.

To the reaction mixture was added 20 grams of anhydrous high surface area potassium fluoride. Stirring was continued for one hour at reflux (135°–140° C.). Ammonia was then bubbled in to convert the pyridine hydrochloride catalyst to ammonium chloride which precipitated. The mixture was filtered hot and the precipitate washed with hot xylene. The combined filtrate was concentrated by distilling out 50 ml of liquid. The mixture wa cooled to 5° C. causing the product 2,2'-ethylidenebis(4,6-di-tertbutylphenyl) fluorophosphite to precipitate (first crop). The mother liquor was further distilled to one-half its volume and a second precipitation carried out (second crop). The precipitates were washed with cold xylene and dried under vacuum at 100° C. The product composition was as follows.

|  | Amount (g) | Yield (%) | G.C. Area Percent | | |
|---|---|---|---|---|---|
|  |  |  | fluoro-phosphite | Bisphenol | hydrogen phos-phonate |
| First Crop | 79 | 71 | 98 | 0.4 | 1.4 |
| Second Crop | 17 | 15 | 93 | 2.5 | 3.6 |
| Composite | 96 | 86 |  |  |  |

EXAMPLE 3

Surprisingly other tert-amines have not shown the catalytic effect of pyridine. This example shows the lack of catalytic effect by triethylamine.

In a reaction flask was placed 2.5 g 2,2'-ethylidenebis (4,6-di-tert-butylphenyl) chlorophosphite, 0.85 g dry KF and 5 ml xylene all under nitrogen. While stirring the mixture was heated to reflux. Samples were taken periodically and analyzed by GC for the corresponding fluorophosphite. At the end of 2 hours the product example solvent analyzed 26 area percent fluorophosphite. At this point, 125 mg of triethylamine hydrochloride was added and stirring continued at reflux. After an additional hour the reaction mixture example solvent analyzed 27 area percent chlorophosphite showing that the triethylamine hydrochloride did not catalyze further reaction.

EXAMPLE 4

In a reaction flask under nitrogen was placed 2.5 g of 2,2'-ethylidenebis (4,6-di-tert-butylphenyl) chlorophosphite, 0.85 g dry KF and 5 ml xylene. While stirring the mixture was heated to 135°. Stirring was continued at 135°–140° C. and a sample was withdrawn and analyzed periodically by GC as follows.

| Component | Percent Composition | | | |
|---|---|---|---|---|
|  | ½ hr | 1 hr | 2 hr[1] | 3 hr |
| chlorophosphite | 74 | 63 | 61 | 51 |
| fluorophosphite | 23.1 | 34.4 | 35.5 | 35.4 |
| hydrogenphosphonate | 3.2 | 3.4 | 3.2 | 4.9 |

[1] A solution of decyl dimethylamine hydrochloride made from 0.2 ml of the amine in xylene was added after taking the 2 hr sample.

This again showed the lack of catalytic affect by a trialkyl amine.

We claim:

1. A process for exchanging a halogen bonded to a phosphorus atom with fluorine said process comprising reacting a phosphorus compound, having 1–2 halogen atoms selected from chlorine, bromine or iodine bonded directly to phosphorus, with a fluoride salt selected from metal fluorides or ammonium fluoride in the presence of a hydrogen halide salt of a pyridine-type compound.

2. A process of claim 1 wherein said halogen atom is chlorine.

3. A process of claim 1 wherein said fluoride salt is an alkali metal fluoride.

4. A process of claim 2 wherein said fluoride salt is an alkali metal fluoride.

5. A process of claim 4 wherein said alkali metal fluoride is potassium fluoride.

6. A process of claim 3 wherein said alkali metal fluoride is potassium fluoride.

7. A process of claim 1 wherein said hydrogen halide is hydrogen chloride.

8. A process of claim 7 wherein said pyridine-type compound is pyridine.

9. A process of claim 8 wherein said halogen atom is chlorine.

10. A process of claim 9 wherein said fluoride salt is an alkali metal fluoride.

11. A process of claim 10 wherein said alkali metal fluoride is potassium fluoride.

12. A process of claim 1 wherein said phosphorus compound has the structure

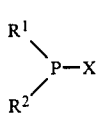  (I)

or

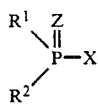  (II)

wherein X is chlorine, bromine or iodine, Z is oxygen or sulphur, $R^1$ is selected from the group consisting of substituted and unsubstituted alkoxy, thioalkoxy, aryloxy, thioaryloxy, cycloalkoxy, alkenoxy, and arylalkoxy and $R^2$ is selected from the same group as $R^1$ or is X, or $R^1$ and $R^2$ can jointly form a substituted or unsubstituted divalent hydrocarbon group bonded at each end through oxygen or sulphur to the phosphorus atom in structures I or II.

13. A process of claim 12 wherein X is chlorine.

14. A process of claim 13 wherein said fluoride salt is an alkali metal fluoride.

15. A process of claim 14 wherein said pyridine-type compound is pyridine.

16. A process of claim 15 wherein said alkali metal fluoride is potassium fluoride and said hydrogen halide is hydrogen chloride.

17. A process of claim 16 wherein $R^1$ and $R^2$ jointly form a divalent hydrocarbon group having the structure

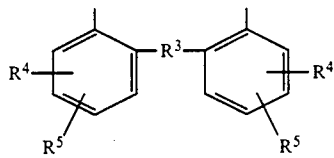

wherein $R^3$ is a methylene or alkylidene bridge or is absent forming a direct ortho-ortho bond between the benzene rings, $R^4$ and $R^5$ are independently selected from alkyl groups, cycloalkyl groups and aralkyl groups and the unsubstituted bond on each benzene ring is bonded through oxygen to said phosphorus atom in structures I or II.

18. A process of claim 17 wherein said hydrocarbon group has the structure

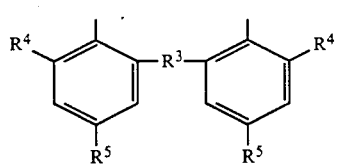

wherein $R^4$ and $R^5$ are alkyl groups.

19. A process of claim 18 wherein $R^4$ and $R^5$ are tertbutyl groups.

20. A process of claim 17 wherein said phosphorus compound has structure I.

21. A process of claim 20 wherein said hydrocarbon group has the structure

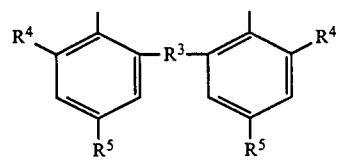

22. A process of claim 21 wherein $R^4$ and $R^5$ are tert-butyl groups.

23. A process of claim 22 wherein $R^3$ is present and is the ethylidene group.

* * * * *

UNITED STATES PATENT AND TRADEMARK OFFICE
CERTIFICATE OF CORRECTION

PATENT NO. : 5,061,818

DATED : October 29, 1991

INVENTOR(S) : Lester P.J. Burton et al.

It is certified that error appears in the above-identified patent and that said Letters Patent is hereby corrected as shown below:

Cover Page, References Cited, the following U.S. Documents should be added:
-- 2,903,474  9/1959  Lanham                  558/84
   2,910,499 10/1959  Lanham                  558/84
   2,922,813  1/1960  Lanham                  558/84
   3,522,331  7/1970  Denver et al.           558/84
   3,914,344 10/1975  Schwarzenbach et al.    558/84 --.

Cover Page, References Cited, the following Foreign Patent Document should be added -- 280938  7/1988  European --.

Cover Page, References Cited, the following Other References should be added -- J.H. Fletcher et al., "The Synthesis of Parathion and Some Closely Related Compounds", J. Amer. Chem. Soc., 72, 2461 (June 1950). --.

Column 8, line 29, reads "tertbutyl groups." and should read -- tert-butyl groups. --.

Signed and Sealed this

Thirteenth Day of April, 1993

Attest:

STEPHEN G. KUNIN

*Attesting Officer*     *Acting Commissioner of Patents and Trademarks*